(12) United States Patent
Willis

(10) Patent No.: US 11,241,182 B1
(45) Date of Patent: Feb. 8, 2022

(54) GEL DISTRIBUTION APPARATUS AND METHOD

(71) Applicant: Forest Devices, Inc., Pittsburgh, PA (US)

(72) Inventor: Dan Willis, Pittsburgh, PA (US)

(73) Assignee: Forest Devices, Inc., Pittsburgh, PA (US)

( * ) Notice: Subject to any disclaimer, the term of this patent is extended or adjusted under 35 U.S.C. 154(b) by 0 days.

(21) Appl. No.: 17/224,187

(22) Filed: Apr. 7, 2021

(51) Int. Cl.
| A61B 5/291 | (2021.01) |
| A61B 5/266 | (2021.01) |
| A61B 5/256 | (2021.01) |
| A61B 5/00 | (2006.01) |

(52) U.S. Cl.
CPC .............. *A61B 5/266* (2021.01); *A61B 5/256* (2021.01); *A61B 5/291* (2021.01); *A61B 5/6803* (2013.01); *A61B 2560/0266* (2013.01); *A61B 2560/0443* (2013.01); *A61B 2562/046* (2013.01)

(58) Field of Classification Search
CPC ...... A61B 5/291; A61B 5/6814; A61B 5/6803
See application file for complete search history.

(56) References Cited

U.S. PATENT DOCUMENTS

| 3,474,775 A | 10/1969 | Johnson |
| 3,508,541 A | 4/1970 | Westbrook et al. |
| 3,602,216 A | 8/1971 | Moe, Jr. et al. |
| 3,776,228 A | 12/1973 | Semler |
| 4,458,687 A | 7/1984 | Dickson |
| 4,632,122 A | 12/1986 | Johansson et al. |
| 4,742,831 A | 5/1988 | Silvian |
| 4,919,148 A | 4/1990 | Muccio |
| 5,078,134 A | 1/1992 | Heilman et al. |
| 5,479,934 A | 1/1996 | Imran |
| 5,689,215 A | 11/1997 | Richardson et al. |
| 6,301,493 B1 | 10/2001 | Marro et al. |
| 6,510,333 B1 | 1/2003 | Licata et al. |
| 6,516,218 B1 | 2/2003 | Cheng et al. |
| 6,574,513 B1 | 6/2003 | Collura et al. |
| 6,640,122 B2 | 10/2003 | Manoli et al. |
| 6,952,605 B1 | 10/2005 | Scarberry |
| 7,367,956 B2 | 5/2008 | King |
| 7,474,918 B2 | 1/2009 | Frantz et al. |
| 7,941,213 B2 | 5/2011 | Markowitz et al. |

(Continued)

FOREIGN PATENT DOCUMENTS

CN 103720470 A 4/2014

*Primary Examiner* — Michael J D'Abreu
(74) *Attorney, Agent, or Firm* — Buchanan Ingersoll & Rooney PC

(57) ABSTRACT

A gel distribution apparatus can include modules so that each module is connected to a respective sensor of a sensor array included in headgear. Each module can be configured to facilitate the distribution of a gel onto a scalp of a patient to permit deployment of the gel at locations on the head of a patient near the sensor to which the module is adjacently positioned or attached. The modules can each include at least one flange to permit a user to pull the module away from the scalp while also pressing a compressible gel reservoir of the module toward the scalp for directing the gel onto the scalp. The pulling force can help counteract internal pressure generated from compression of the reservoir to expel the gel so that the gel flows along a desired gel flow path without excessive back pressure.

20 Claims, 11 Drawing Sheets

(56) References Cited

U.S. PATENT DOCUMENTS

| | | |
|---|---|---|
| 8,265,736 B2 | 9/2012 | Sathaye et al. |
| 8,444,559 B2 | 5/2013 | Fink et al. |
| 8,663,121 B2 | 3/2014 | Stickney et al. |
| 2007/0255127 A1 | 11/2007 | Mintz et al. |
| 2007/0272313 A1 | 11/2007 | Olds |
| 2008/0009763 A1 | 1/2008 | Chiou et al. |
| 2010/0036275 A1 | 2/2010 | Alkire |
| 2010/0137708 A1 | 6/2010 | Tamura et al. |
| 2011/0245707 A1 | 10/2011 | Castle et al. |
| 2012/0022349 A1 | 1/2012 | Poupko et al. |
| 2012/0107811 A1 | 5/2012 | Kelso et al. |
| 2012/0143020 A1 | 6/2012 | Bordoley et al. |
| 2013/0023748 A1 | 1/2013 | Afanasewicz et al. |
| 2014/0142410 A1 | 5/2014 | Erb et al. |
| 2014/0243643 A1 | 8/2014 | Sunderland |
| 2015/0065838 A1 | 3/2015 | Wingeier et al. |
| 2015/0112153 A1 | 4/2015 | Nahum |
| 2015/0313498 A1 | 11/2015 | Coleman et al. |
| 2016/0022165 A1 | 1/2016 | Sackellares et al. |
| 2016/0022981 A1 | 1/2016 | Wingeier et al. |
| 2016/0144186 A1 | 5/2016 | Kaemmerer et al. |
| 2016/0235322 A1 | 8/2016 | Alkire |
| 2016/0287127 A1 | 10/2016 | Kesinger et al. |
| 2016/0346534 A1 | 12/2016 | Isaacson et al. |
| 2017/0281036 A1* | 10/2017 | Parvizi .................. A61B 5/325 |
| 2018/0165923 A1 | 6/2018 | Schmitt et al. |
| 2019/0021664 A1 | 1/2019 | Kesinger et al. |
| 2020/0237248 A1 | 7/2020 | Willis et al. |

\* cited by examiner

GEL DISTRIBUTION APPARATUS AND METHOD

FIELD

The present innovation relates to devices that can be utilized to apply a gel to one or more sensors and a patient's scalp to help form sufficient electrical connections for the measurement of health metrics of a patient. The present innovation also relates to methods of making and using such devices and applying gel onto the scalp of a patient for use in conjunction with medical related measurements that can be made using one or more sensors.

BACKGROUND

A headband in which electrodes are in fixed positions can be used to position electrodes on the head of a patient. The electrodes are often intended to be placed so they will fall in all the positions described in the 10/20 montage. Other headgear in which electrodes can be included are disclosed in U.S. Patent Application Publication Nos. 2019/0021664, 2016/0235322 and 2010/0036275. Electrode configurations and uses can also be appreciated from U.S. Patent Application Publication Nos. 2020/0237248, 2017/0281036, 2016/0346534, 2016/0287127, 2016/0144186, 2016/0022981, 2015/0313498, 2015/0112153, 2014/0142410, 2014/0243643, 2013/0023748, 2012/0143020, 2012/022349, 2011/0245707, 2010/0137708, 2007/0272313, and 2007/0255127 and U.S. Pat. Nos. 3,474,775, 3,602,216, 3,776,228, 4,458,687, 4,742,831, 4,919,148, 5,689,215, 6,516,218, 6,640,122, 6,952,605, 7,367,956, 7,474,918, 7,616,980, 7,941,213, 8,265,736, 8,444,559, and 8,663,121.

SUMMARY

Gel distribution apparatuses for headgear and methods of using and making such apparatuses are provided herein. In some embodiments, the gel distribution modules can be provided for positioning adjacent to and/or in connection with respective sensors of a sensor array for headgear. There may be a gel distribution module attached to and/or positioned adjacent to a respective one of each and every one of the sensors of the sensor array in some embodiments so that the gel can be applied to a patients scalp on and near each sensor individually at different times by a user.

A gel distribution module for headgear is provided. In a first aspect, the gel distribution module can include an inner component having a gel conduit defining a gel passageway that extends from a gel inlet opening to a gel outlet opening, a gel receptacle having a gel reservoir that is compressible from an initial position to a compressed position in response to application of a compression force, and an outer component having an annular body that defines an inner hole and at least one flange extending away from the inner hole. The gel receptacle can be positioned to extend from the inner hole and the gel receptacle can also be positioned between the inner component and the outer component. The inner component can be positionable adjacent an inner side of a body of the headgear and the outer component can be positionable on an exterior side of the body of the headgear for connection with the inner component.

In a second aspect, the inner component can have a piercing member positioned adjacent to the gel inlet opening configured to form a punctured opening so gel from the gel reservoir is passable from the gel reservoir through the gel inlet opening in response to the compression force meeting or exceeding a puncture threshold. In a third aspect, the at least one flange can extend beyond the gel receptacle. In a fourth aspect, the gel conduit can also include at least one secondary passageway in fluid communication with the gel passageway so that gel is passable through each secondary passageway in a secondary flow direction that is transverse to a primary flow direction of gel passing through the gel passageway to the gel outlet opening.

In a fifth aspect, the gel distribution module can include a gel seal member that is positioned to help enclose the gel reservoir and is positioned between the inner component and the gel reservoir. In a sixth aspect, the inner component can have a piercing member positioned adjacent to the gel inlet opening configured to form a punctured opening in the gel seal member attached to the gel receptacle to enclose the gel reservoir so gel from the gel reservoir is passable from the gel reservoir through the gel inlet opening in response to the compression force meeting or exceeding a puncture threshold.

It should be appreciated that in yet other aspects of the gel distribution module, the first aspect can be combined with only the second aspect, only the third aspect, only the fourth aspect, only the fifth aspect, or only the sixth aspect or a combination of any of the second through sixth aspects to form yet other embodiments of the gel distribution module.

A headgear is also provided. An embodiment of the headgear can include an embodiment of the gel distribution module. For instance, the headgear can include one or more of a particular embodiment of the gel distribution module discussed above or discussed elsewhere herein.

In a first embodiment, the headgear can include a body having an array of sensors. The body can be attached to a plurality of gel distribution modules so that each of the gel distribution modules is positioned adjacent to a respective sensor of the array of sensors, each of the gel distribution modules can be a gel distribution module of the first through seventh aspects discussed above or a combination of such aspects.

In some embodiments, the body can be comprised of fabric and the headgear can also include at least one strap or cord.

Methods of applying gel onto a patient to use headgear to measure biosignals of the patient is also provided. In a first aspect of the method, the method can include providing headgear having a plurality of sensors and gel distribution modules. Each of the gel distribution modules can be attached to a body of the headgear adjacent a respective sensor of the plurality of sensors. The method can also include applying a compression force to a gel receptacle of a first gel distribution module of the gel distribution modules to form a punctured opening for outputting gel from the gel distribution module to a scalp of the patient wearing the headgear to apply the gel to the scalp of the patient and applying a pulling force that is opposite the compression force on the first gel distribution module via at least one flange of the first gel distribution module at the same time the applying of the compression force is performed.

Embodiments of the method can also include connecting the headgear to a computer device to use the sensors to measure the biosignals of the patient. The sensors can measure the biosignals to detect whether the patient experienced a stroke.

Embodiments of the method can utilize an aspect of the above discussed gel distribution modules. For example, each of the gel distribution modules can include an inner component having a gel conduit defining a gel passageway that extends from a gel inlet opening to a gel outlet opening, a gel receptacle having a gel reservoir that is compressible from an initial position to a compressed position in response to application of the compression force, and an outer component having an annular body that defines an inner hole and at least one flange extending away from the inner hole. The gel receptacle can be positioned to extend from the inner hole and the gel receptacle can be positioned between the inner component and the outer component. The inner component can be positionable adjacent an inner side of a body of the headgear and the outer component can be positionable on an exterior side of the body of the headgear for connection with the inner component. The inner component can include a piercing member positioned adjacent to the gel inlet opening that is configured to form a punctured opening in a gel seal member positioned to enclose the gel reservoir so gel from the gel reservoir passes from the gel reservoir through the gel inlet opening in response to the compression force meeting or exceeding a puncture threshold. The applied compression force can meet or exceed the puncture threshold to form the punctured opening for outputting the gel from the gel reservoir. The applying of the pulling force utilized in the method can include gripping the at least one flange to pull on the at least one flange to apply the pulling force. The gel conduit can also include at least one secondary passageway in fluid communication with the gel passageway so that gel is passable through each secondary passageway in a secondary flow direction that is transverse to a primary flow direction of gel passing through the gel passageway to the gel outlet opening. The gel that is output from the first gel distribution module can pass through the gel passageway and the at least one secondary passageway to contact the scalp and the sensor to which the first gel distribution module is adjacently positioned.

In embodiments of the method, the gel distribution modules can be configured so that the at least one flange extends beyond the gel receptacle for each module.

In embodiments of the method, the headgear can include conductive connectors that connect the sensors to a communication connector. The communication connector can be configured to connect the headgear to a computer device so that sensor data collected from the sensors can be communicated to the computer device. The computer device can be configured to utilize that data to detect a condition of the patient wearing the headgear.

Other details, objects, and advantages of apparatuses for gel distribution, gel distribution mechanisms, headgear, neurological condition detection devices, and methods of making and using the same will become apparent as the following description of certain exemplary embodiments thereof proceeds.

BRIEF DESCRIPTION OF THE DRAWINGS

Exemplary embodiments of apparatuses for gel distribution, headgear, electrodes, sensor arrays, gel distribution mechanisms (e.g. gel distribution modules), neurological condition detection mechanisms, and methods of making and using the same are shown in the accompanying drawings. It should be understood that like reference numbers used in the drawings may identify like components.

DETAILED DESCRIPTION

Figure 1:
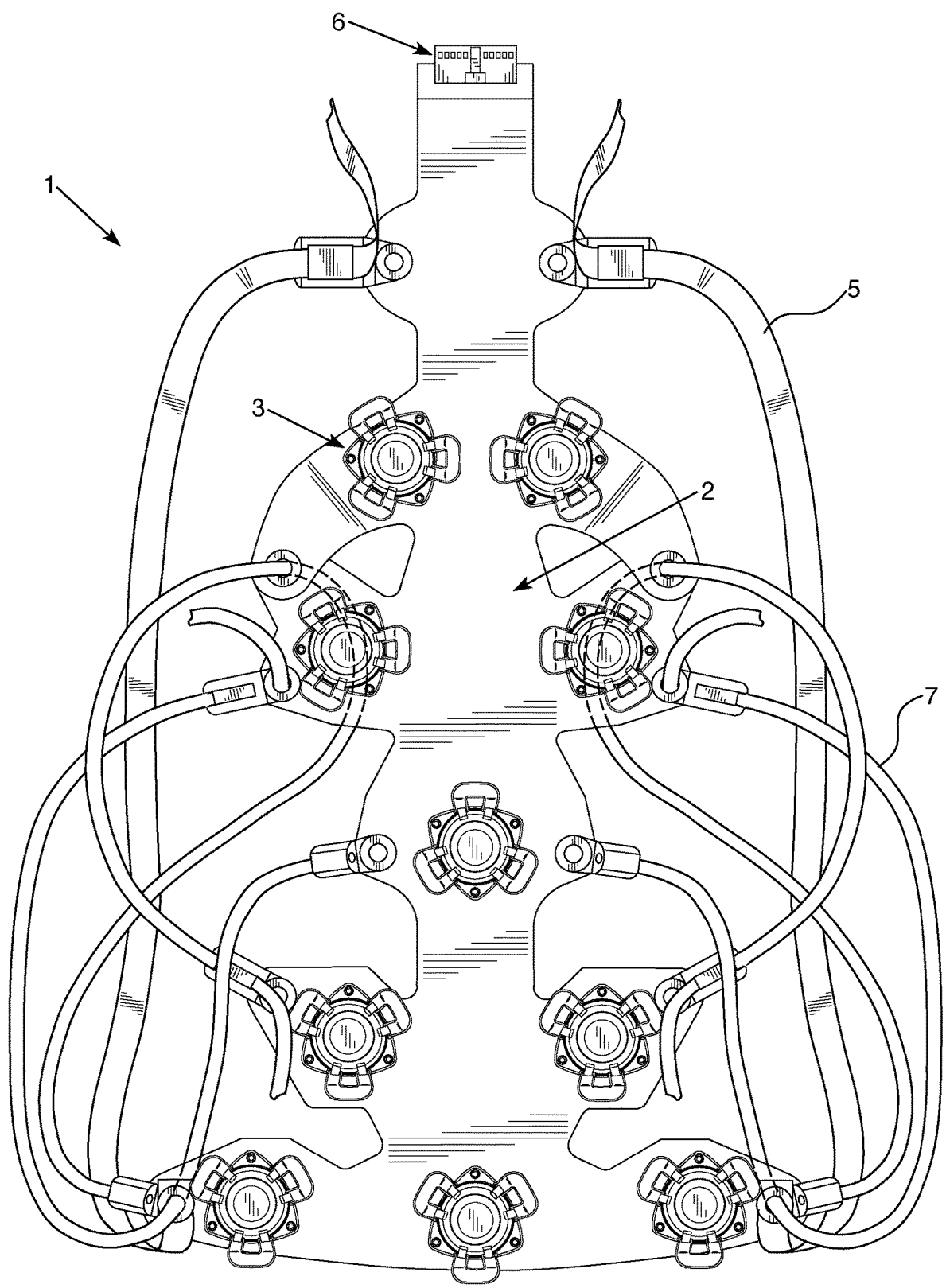
FIG. 1 is a perspective top view of a first exemplary embodiment of headgear having an exemplary embodiment of a gel distribution apparatus that includes gel distribution modules 3 attached to the body 2 of the headgear 1.
Figure 2:
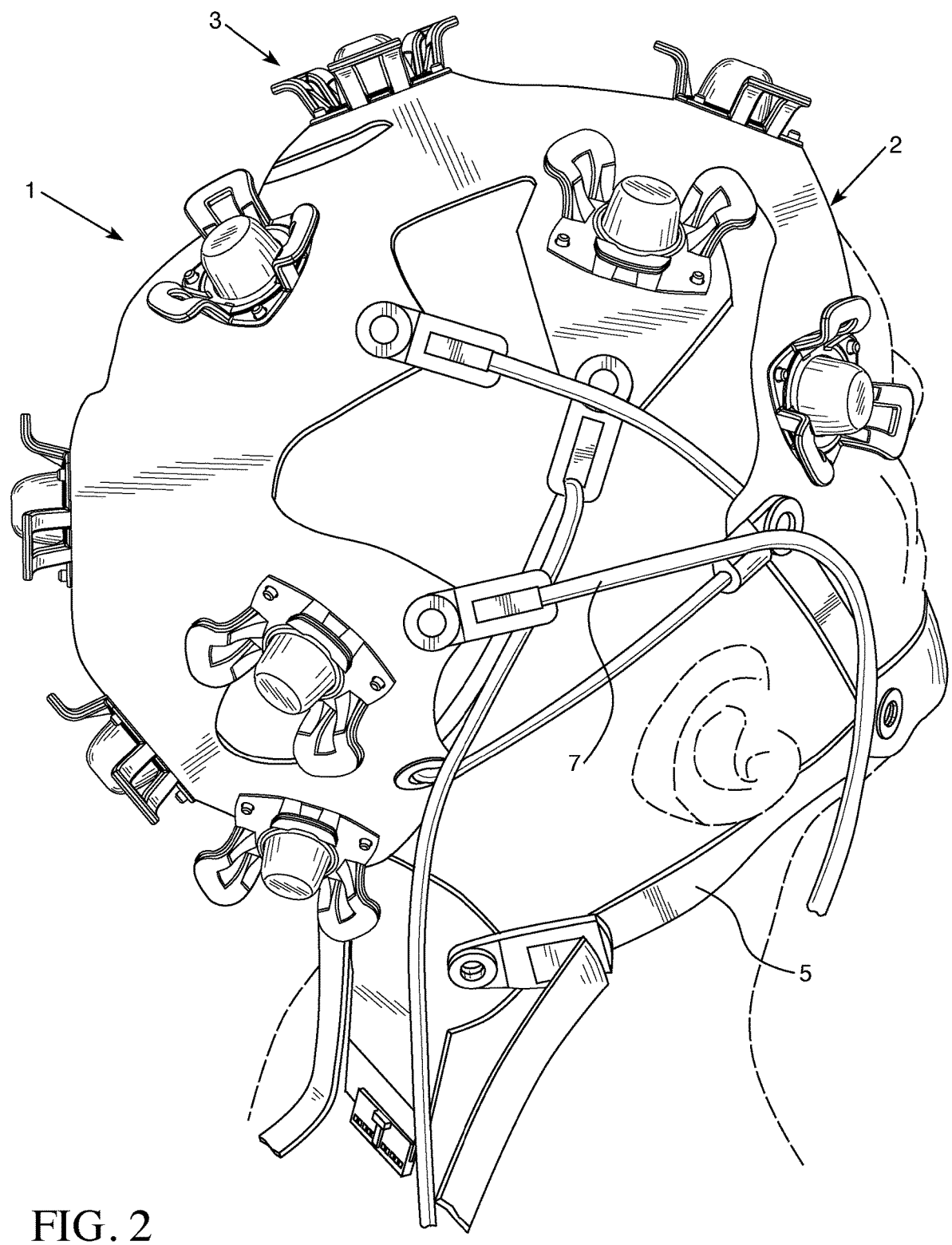
FIG. 2 is an elevated rear right side perspective view of the first exemplary embodiment of the headgear 1 being worn by a patient. An elevated rear left side perspective view of the first exemplary embodiment of the headgear 1 being worn by a patient would be a mirror image of FIG. 2.

Referring to FIGS. 1-12, an exemplary embodiment of headgear 1 can have a sensor array 24 can include a body 2. The body 2 can be comprised of fabric or a fabric type material. For example, the body can be formed from cotton, polyester, cotton and polyester blended fabric, nylon, flax, rayon, viscose, material composed of regenerated cellulose fibers, wool, bamboo, texliner mesh, hemp, leather, fish leather, lyocell, another other type of fabric material or textile type material and combinations thereof. The body 2 can alternatively be composed of a semi-rigid plastic in some less preferred embodiments.

The body 2 can include conductive connectors 8. Each conductive connector 8 can be comprised of a body that is structured as an elongated member that is composed of metal or other electrically conductive material that can convey an electrical signal and/or other data from the sensor(s) to which that conductive connector 8 is attached to a communication connector 6 for transmission of the signal and/or other data of a sensor 4 of sensor array 24 to a computer device (e.g. a neurological condition detection unit, a stroke detection device, etc.). The computer device can be configured to evaluate the data from the sensor array and evaluate whether the patient has undergone a stroke or has experienced another type of neurological injury.

Each conductive connector 8 can have at least two terminal ends—a first terminal end and a second terminal end opposite the first terminal end. The communication connector 6 can be attached to first terminal ends of the conductive connectors 8 adjacent to or at a rear of the body 2 that is opposite the front of the body 2. The communication connector 6 can be a separate element connected to first terminal ends of the conductive connectors 8 to facilitate a connection with wiring, cabling, or other communication connection device (e.g. transceiver unit, a universal serial bus ("USB") connection, etc.). In some embodiments, it is contemplated that fabric material of the body 2 can be hardened to define the communication connector 6 at the rear of the body at which first terminal ends of the conductive connectors 8 are positioned for connection to another element. Each conductive connector 8 can be positioned on the body 2 so that its second terminal end can be connected to a respective sensor 4 (e.g. terminating at the sensor, conductively connected to the sensor, etc.).

The sensor 4 can be configured as an electrode or other type of sensor (e.g. a detector) that can detect and/or measure brain waves of a patient or other biosignals of a patient. The sensor 4 can have a body that has an annular shape that includes an inner hole 4a or can be a non-annular structure (e.g. a disc, a plate, etc.).

In some embodiments the communication connector 6 can be used in conjunction with a security chip to prevent fraudulent copies of the head gear from being improperly utilized. In another embodiment, the communication connection 6 can be used with a security chip or identification chip to prevent unauthorized use and/or record the number of uses of the sensor array 24 or headgear 1.

The body 2 of the headgear 1 can be configured so that it is wearable on the head of a patient. FIGS. 2 and 10-12 illustrate an example of a patient wearing the headgear 1 on the patient's head. The headgear 1 can include straps 7 and other types of elongated elements, such as cords 5, to help position the headgear on the patient's head and sufficiently tighten the headgear on the head so that the sensors 4 can be placed into contact with the scalp of the patient's head or be positioned adjacent to the patient's scalp (e.g. within a millimeter (mm) of being in contact with the patient's scalp, within 4 mm of contacting the patient's scalp, within 6 mm of contacting the patient's scalp, etc.). The headgear can also include a chin strap that is attached to the body 2 for providing a tight connection with the patient's chin for helping to position and sufficiently tighten the headgear 1 on the patient's head for positioning of the sensors in pre-selected positions about the patient's head for measuring biosignal data or other health metric data from the patient via the sensors 4 so that such measurement data obtained by the sensors 4 can be provided to at least one computer device via the conductive connectors 8 and communication connector 6 communicatively connected to the sensors 4. The computer device can then utilize that data to evaluate at least one medical condition of the patient.

The body 2 of the headgear 1 can have sensors 4 positioned on an internal side of the body 2 that is to be directly contacting the head of a patient when the patient wears the headgear. The opposite side of the body 2 can be an external side that is opposite the internal side. The external side can face away from the patient's head when the headgear is worn on the patient's head. The sensor array 24 can include a plurality of sensors 4. Each sensor 4 can be connected to a respective one of the conductive connectors 8 so that measurement data collected by the sensor can be transmitted to the communication connector 6 for sending to at least one computer device connected to the communication connector 6 (e.g. there can be a respective conductive connector for a respective one of the sensors 4 of the sensor array 24).

The headgear 1 can also include a gel distribution apparatus that includes a plurality of gel distribution modules 3. The distribution modules can include a first distribution module, second distribution module, third distribution module, a fourth distribution module, as well as other distribution modules such that there is a respective distribution module for each sensor 4 of the sensor array 24 or at least a gel distribution module for a pre-selected number of the sensors 4 of the sensor array 24.

For example, there can be a respective gel distribution module 3 that is attached to or otherwise adjacently positioned to a respective sensor 4 of the sensor array 24 so that each sensor 4 has its own respective gel distribution module 3. Each gel distribution module 3 can be a device configured to store gel and facilitate the output of the stored gel onto the scalp of a patient's head and/or onto the sensor 4 to which the gel distribution module is attached or otherwise adjacently positioned to help facilitate the formation of a sufficiently strong electrical connection between the sensor and the patient's scalp to help ensure that the sensor can obtain measurement data from the patient of a sufficiently high quality. The gel can be can be a silver chloride gel (e.g. an AgCl gel, a mixture that includes AgCl and water that forms a gel or slurry at room temperature, etc.). The gel could alternatively be another type of electrical conduction connection enhancement gel.

Each gel distribution module 3 can include an external component 3b that includes at least one flange 3c extending from an annular body that defines an inner hole 3d. The inner hole 3d can be circular in shape or have another type of shape (e.g. polygonal shape, triangular in shape, an irregular shape, an oval shape, etc.). The external component 3b can be positionable adjacent to and in contact with the exterior surface of the exterior side of the fabric body 2 of the headgear 1 when attached to the body 2 of the headgear 1.

A gel receptacle 3a can be positionable within the hole 3d of the annular body of the exterior component 3b and/or extend through the hole 3d and can be positioned to extend from the inner hole 3d outwardly away from the body 2 of the headgear and the patient's head when the patient is wearing the headgear 1 on his or her head. The gel receptacle 3a can be a domed shaped element that is sized and configured to at least partially define a collapsible reservoir that retains gel 3e therein for release and expelling toward a scalp of a patient. In some embodiments, the gel receptacle 3a can be structured as a flanged cup, a flanged dome, or another type of flanged gel retaining body having a gel reservoir for retaining gel 3e for storing the gel 3e until a user desires to apply the gel to a sensor 4 and/or the scalp S of a patient.

The gel 3e stored in the gel reservoir 3gr of the gel receptacle 3a can be a slurry or aqueous solution that can be stored in the gel reservoir 3gr of the gel receptacle 3a. When stored in the gel reservoir 3gr of the gel receptacle, the gel 3e can be filled within the reservoir to have a shape that is defined by the shape of the gel reservoir 3gr.

After the gel reservoir is filled with gel 3e, a gel seal member 3f can be attached to the body of the gel receptacle 3a to cover the opening of the gel reservoir 3gr defined by the gel receptacle 3a to fully enclose the gel 3e within the gel receptacle reservoir 3gr for storage of the gel 3e. After the gel seal member 3*f* is attached to the gel receptacle 3*a* for retaining the gel within the gel reservoir 3*gr*, the gel receptacle 3*a* and gel seal member 3*f* assembly can be positioned between the outer component 3*b* and the inner component 3*g* for forming the gel distribution module 3. In so positioning the gel receptacle 3*a* and gel seal member 3*f* assembly, the gel seal member 3*f* can be positioned so a first side of the gel seal member contacts a portion of the fabric body 2 of the headgear while a second side that is opposite its first side contacts the gel within the gel reservoir of the gel receptacle 3*a*. The gel seal member 3*f* can be positioned on or adjacent the fabric body 2 so that it is aligned with a sensor 4 attached to the body 2 and/or an inner hole 4*a* defined by the body of the sensor 4 incorporated into the body 2 of the headgear 1 (e.g. sensor 4 attached to the body 2, printed on the inner side of the body 2, etc.)

The gel receptacle 3*a* can be composed of a deformable material such as an elastomeric material or a polymeric material that defines a domed shaped cavity or domed shape opening for the gel reservoir 3*gr*. The body of the gel receptacle 3*a* can include an inner flange element 3*fe* that extends from the gel reservoir 3*gr* to facilitate attachment of the gel receptacle 3*a* between the annular body of the exterior component 3*b* and a body of an inner component 3*g*.

The inner flange element 3*fe* of the gel receptacle 3*a* can also (or alternatively) be sized and configured to attachment to a gel seal member 3*f* so that the gel seal member 3*f* is attached to the inner flange element 3*fe* and covers an inner opening of the gel reservoir to help retain the gel within the gel receptacle until the gel distribution module is actuated to expel the gel toward the scalp of a patient wearing the headgear 1. The gel seal member 3*f* can have a shape that is to mirror the shape of the inner opening of the gel reservoir defined by the gel receptacle 3*a* to cover the entirety of the inner opening and fully enclose gel 3*e* positioned within the gel reservoir 3*gr* of the gel receptacle 3*a* so that the gel is storable within the gel reservoir 3*gr*.

The inner component 3*g* of the gel distribution module 3 can include a body having one or more projections 3*h* that extend from an outer side of the body of the inner component for passing through openings 3*w* defined in the annular body of the outer component 3*b* for attachment of the inner component 3*g* to the outer component 3*b*. The openings 3*w* and projections 3*h* can be positioned so that they are located around a periphery of the body of a sensor 4 when the inner and outer components 3*g* and 3*b* are connected together to attach the gel distribution module to the body 2 of the headgear and be positioned adjacent to and/or attached to the sensor 4.

In some embodiments, each projection 3*h* can be heat staked, welded, melted, bonded, joined, fastened, or otherwise coupled to the annular body after the projections 3*h* are passed through the attachment openings 3*w* of the annular body of the outer opponent 3*b* for attachment of the inner and outer components 3*g* and 3*b*. Such attachment may occur after the gel receptacle 3*a* having a filled gel reservoir 3*gr* and gel seal member 3*f* attached thereto are positioned between the inner and outer components 3*g* and 3*b*. The outer component 3*b*, gel receptacle 3*a*, and gel seal member 3*f* can be located adjacent an exterior surface of the body 2 (e.g. on the exterior surface of the body 2 or adjacent the exterior surface) while the inner component 3*g* is located on an inner surface of the body 2 adjacent to a sensor 4 for such positioning, as may best be seen from FIG. 4. The projections 3*h* can then be passed through holes 2*b* in the body 2 and passed through holes 3*w* in the outer component 3*b* for attachment of the inner component 3*g* to the outer component 3*b*, which can also couple the gel receptacle 3*a*, gel seal member 3*f*, and fabric body 2 to these components form the gel distribution module 3 and position the gel distribution module 3 adjacent a sensor 4 and/or attach the module to the sensor 4 via its contact with the inner component 3*g* and attachment of the inner component 3*g* to the outer component 3*b* by having projections 3*h* pass through holes 2*b* in the body 2 and attachment holes 3*w* of the outer component 3*b* for attachment to the outer component 3*b*.

The outer side of the inner component 3*b* can be positioned to face toward a sensor 4 attached to the body 2 or to be positioned for contact with the sensor 4. The inner component 3*g* can also include an inner side 3*m* that is opposite its outer side that is positionable for contacting a patient's head or being positioned on or near the scalp S of a patient when the gel distribution module 3 is attached to the body 2 of the headgear 1 and the headgear 1 is worn by the patient.

A central portion or middle portion of the inner component 3*g* can define a gel inlet opening 3*j* of a gel passageway 3*o* defined in a gel conduit 3*k* that extends from the inner component 3*g*. The gel conduit 3*k* can extend away from the inner side 3*m* of the body of the inner component 3*g* and be attached to the inner component 3*g* or be an integral portion of the inner component 3*g*. The gel conduit 3*k* can be positioned to extend away from the inner component 3*g* toward the scalp S of the patient when the headgear 1 is worn by the patient (e.g. on the patient's head).

The gel inlet opening 3*j* can be aligned with and in fluid communication with a gel passageway 3*o* defined by the gel conduit 3*k* that extends from the gel inlet opening 3*j* to a gel outlet opening 3out defined at the distal end 3*y* of the gel conduit 3*k*. The gel conduit 3*k* can define the gel passageway 3*o* to extend from its inlet and away from the gel receptacle 3*a*. For instance, the gel passageway 3*o* can extend from the gel inlet opening 3*j* a to its gel outlet opening 3out. The gel outlet opening 3out can be positioned to expel gel from the gel passageway 3*o* toward the scalp S of a patient when the headgear 1 is worn on the patient's head.

In some embodiments, the gel conduit 3*k* can be tapered so that its distal end 3*y* from which gel is passable via the outlet 3out of the gel pathway 3*o* defined at the distal end 3*y* of the gel conduit 3*k* is smaller in area than its more proximal end positioned adjacent the gel inlet opening 3*j* of the gel conduit 3*k*. In other embodiments, the gel conduit 3*k* may define a gel passageway 3*o* having a uniform cross-sectional area or may be a flared distal end 3*y* that has an outlet that has a larger area than the area of the gel inlet opening 3*j*.

The gel conduit 3*k* can also have one or more secondary passageways 3*p* that extend away from the gel passageway 3*o* to laterally distribute the gel to other locations in other directions from the gel outlet 3out. For instance, the one or more secondary passageways 3*p* can be defined in the gel conduit 3*k* so that gel is passed through each secondary passageway 3*p* in a secondary flow direction that is transverse (e.g. perpendicular, within 10° of being perpendicular, within 15° of being perpendicular, within 30° of being perpendicular within 45° of being perpendicular, etc.) to a primary flow direction of the gel passing through the gel passageway 3*o* for being output from the gel outlet opening 3out at the distal end 3*y* of the gel conduit 3*k*. Each secondary passageway 3*p* can have an inlet that is in fluid communication with the gel passageway 3*o* and have an outlet that is defined in an outer sidewall 3*ks* of the gel conduit 3*k*.

The body of the gel receptacle 3*a* can be configured to be compressible from an initial position in which the gel reservoir 3*gr* has a first volume (or an initial volume) of space to retain the gel therein to a compressed position that reduces the volume of the gel reservoir 3*gr* to a second volume that is smaller than the first volume to push gel 3*e* out of the gel reservoir 3*gr* and into the gel conduit 3*k*.

The inner component 3*g* can include a gel seal piercing member 3*i* that is positioned on the outer side of the inner component and is positionable to be adjacent to or in contact with the gel seal member 3*f*. The gel seal member 3*f* and the gel seal piercing member 3*i* can each be sized and configured so that the gel seal member 3*f* remains intact and does not leak or break when near or touching the gel seal piercing member 3*i* until a force is applied on the gel seal member 3*f* that pushes the gel seal member 3*f* into a sufficient contact with the gel seal piercing member 3*i* that exceeds a puncture threshold for piercing the gel seal member 3*f*. This force can be provided by a user pressing or pushing on the deformable, collapsible gel receptacle 3*a* to provide a compression force CF until the force applied on the gel seal member 3*f* is at or exceeds the puncture pressure for pushing the gel seal member 3*f* through the gel seal piercing member 3*i* to form a punctured opening 31. The puncturing of the gel seal member 3*f* opens the gel reservoir 3*gr* so that gel can pass out of the gel reservoir and through the punctured opening 31 formed by the gel seal piercing member 3*i*. The gel seal piercing member 3*i* can be contoured to help direct the flow of gel toward the gel inlet opening 3*j*, which is positioned to be aligned with the punctured opening formed in the gel seal member 3*f* so that the gel reservoir is in fluid communication with the gel passageway 3*o* of the gel conduit 3*k* and all secondary passageways 3*p* defined in the gel conduit 3*k*.

The gel output from the gel reservoir via the puncturing of the gel seal member 3*i* can be a flow of gel that defines a continuous bead of gel GB that extends from the gel reservoir 3*gr* through the gel passageway 3*o* and secondary passageway(s) 3*p* to a gel distribution area GAD on the scalp S of the patient that is around the outer periphery of the gel conduit 3*k* and second side 3*m* of the inner component 3*g* as well as extending to the body of the sensor 4 for contact therewith. The formed bead of gel GB can provide a conductive connection from the sensor 4 to the scalp S to help improve the quality and sensitivity of the measurement data collectable by the sensor 4, which can be configured to measure electrical biosignals of the patient's head (e.g. brain waves). For instance, the sensors 4 can be electrodes that can measure electrical signals generated by neurons in the patient's head and the measurement sensitivity and quality can be improved via the improved electrical connection that can be provided by the bead of gel formed be outputting of the gel from the gel reservoir to the scalp S and sensor 4 via the gel passageway 3*o* and at least one secondary passageway 3*p*.

Figure 7:
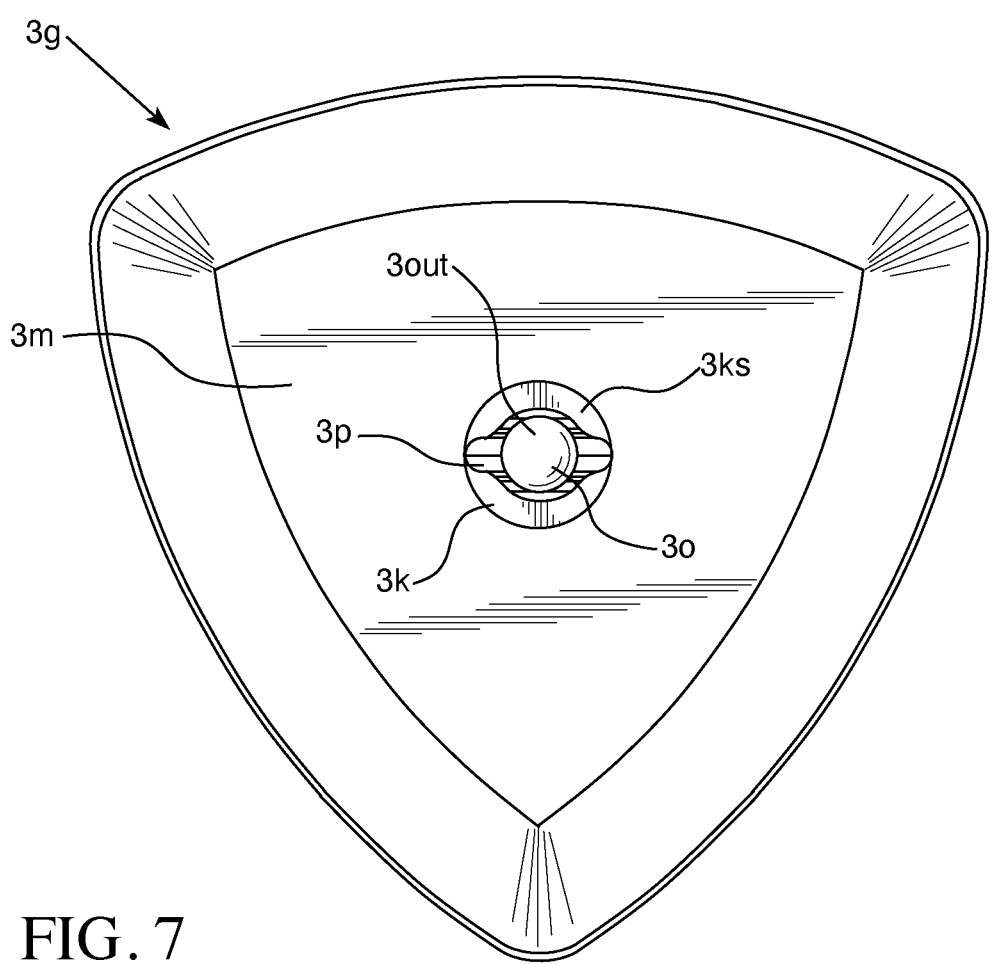
FIG. 7 is a bottom view of the exemplary embodiment of the inner component 3g of the gel distribution module 3 included in the first exemplary embodiment of headgear 1.
Figure 8:
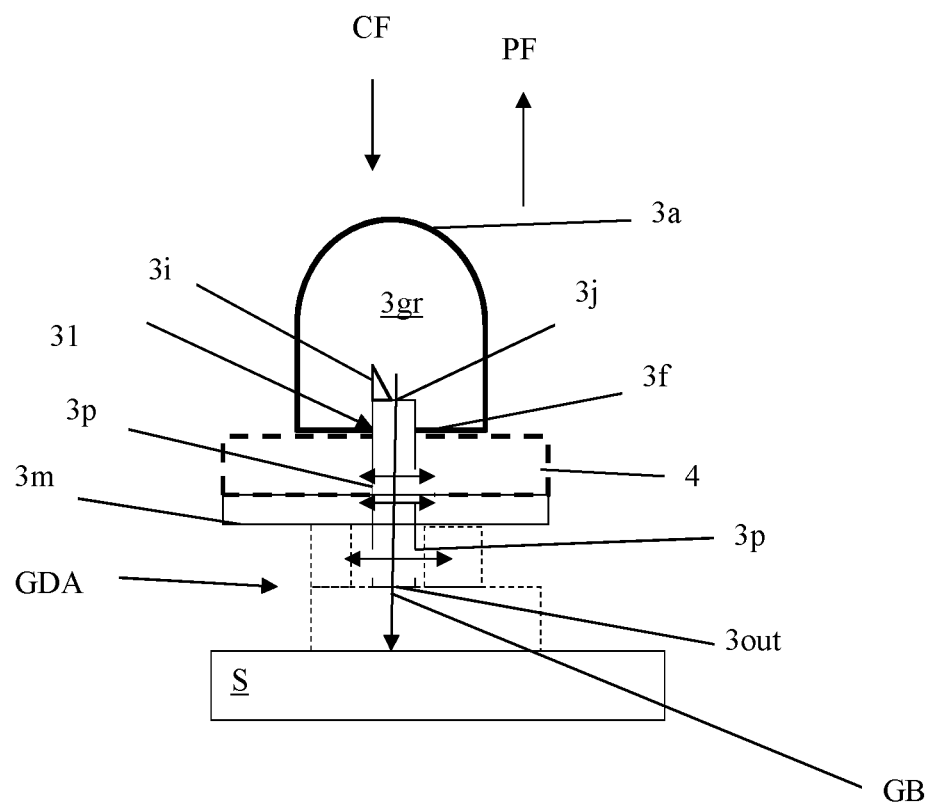
FIG. 8 is a schematic diagram illustrating exemplary gel flow pathways defined by the exemplary embodiment of the gel distribution module included in the first exemplary embodiment of headgear.

As may best be appreciated from FIGS. 7 and 8, in some embodiments, at least one of the secondary passageways 3*p* can output gel from the gel reservoir so that a portion of the gel contacts a body of a sensor 4 positioned between the inner component 3*g* and the outer component 3*b*. One or more of the secondary passageways 3*p* can also be positioned and oriented to output gel laterally along the inner side 3*m* of the inner component in a direction that flows laterally away from the gel conduit 3*k*. Lateral output of the gel for contact with the sensor body while also providing gel to be output via the gel outlet 3out at the distal end 3*y* and outlets of the secondary passageways 3*p* can help provide a continuous trail of gel from the sensor body to direct contact with the scalp of the patient that can help facilitate formation of a bead of gel GB that can provide a stronger electrical connection between the patient's scalp and the sensor 4.

The bead of gel GB provided by the output of gel from the gel reservoir through the gel passageway 3*o* and one or more secondary passageways 3*p* can extend from the sensor body of the sensor 4 to the scalp via the gel passageway 3*o* and at least one secondary passageway 3*p* being in fluid communication with each other. The bead of gel can also include a flared portion of gel that extends about the gel distribution area GDA around the inner side 3*m* of the inner component 3*g* that encompasses a flow path of gel from the distal end 3*y* of the gel conduit and peripherally around that distal end 3*y* via the lateral output of gel provided by at least one secondary passageway 3*p* or multiple secondary passageways 3*p*.

The flanges 3*c* of the outer component 3*b* can help facilitate puncturing of the gel seal member 3*f* in a desired location at or near the gel seal piercing member 3*i* for passing the gel from the gel reservoir to the gel passageway 3*o* and secondary passageway(s) 3*p* via the gel inlet opening 3*j* adjacent to the gel seal piercing member 3*i*. For instance, back pressure can be created from the compression of the gel receptacle 3*a* that causes the gel seal member 3*f* to be punctured via the gel seal piercing member 3*i*. In some instances, the back pressure can result in undesired punctures of other areas of the seal member 3*f* or leaking of the seal member 3*f* or the breaking of another part of the gel receptacle 3*a* forming the gel reservoir. Such undesired leakage of gel can result in lost gel or a failure of gel to form a desired gel area distribution GAD on the scalp S for forming a sufficiently strong electrical connection between the sensor 4 and the scalp S. Avoiding such problems that can be caused by the back pressure that can occur from compression of the gel reservoir to a smaller volume that occurs via pushing or pressing of the gel receptacle 3*a* to its compressed position can be provided by a user providing a pulling force PF on the gel distribution module at the same time that the gel reservoir compression force CF is provided via the pushing or pressing of the gel receptacle 3*a*. The pulling force PF can be provided in a direction that is opposite the direction the compression force CF is provided to help alleviate back pressure issues and help ensure the gel output from the gel reservoir 3*gr* is output from the punctured opening 31 formed by the gel seal piercing member 3*i* and not at other unintended locations that can result in undesired leakage.

The outer component 3*b* can include a single flange or multiple spaced apart flanges 3*c* to help a user provide a pulling force PF while also providing the compression force CF. An example of one or more flanges 3*c* that can be provided to help a user provide a pulling force PF while he or she also applies a compression force CF may best be seen in FIG. 5. The flanges 3*c* can include at least one leg 13 that extends away from the annular body of the inner component 3*b* that defines the inner hole 3*d*. A handle 14 can be defined at a distal end of the flange 3*c*. An intermediate portion 15 of the flange can be positioned between the handle and the at least one leg 13 and be angled, rounded, or bent so that the handle 14 extends laterally away from the inner hole 3*d* and leg(s) 13 of the flange to provide a surface on which a user can grip for applying the pulling force. For instance, the handle 14 can be structured so a user can place one or more fingers under the handle 14 to pull the flanges away from the inner component 3*g* at the same time the user uses another finger (e.g. the user's thumb) or other hand to press or push on the gel receptacle 3*a* to provide the compression force CF for forming the punctured opening 31 and outputting gel from the gel reservoir to form the bead of gel GB.

Each flange 3c can include a single leg 13 or multiple legs 13. When multiple legs 13 are utilized, the legs 13 for each flange 3c can be spaced apart from each other by a space 16, which can be defined by the legs 13 and handle 14. The formed space 16 can provide space for a user's finger or other part of the user's hand and/or can be provided to reduce the mass of the outer component 3b.

Figure 3:
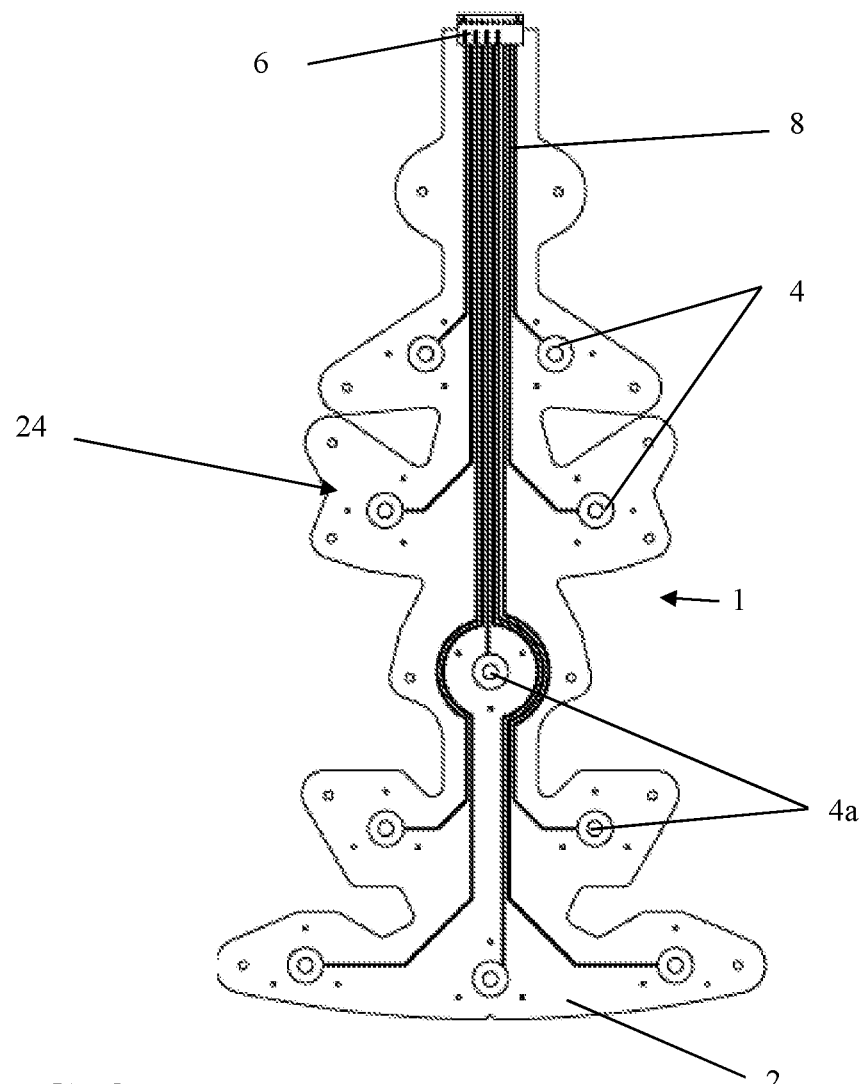
FIG. 3 is a bottom view of the body 2 of the first exemplary embodiment of headgear 1 illustrating sensors 4 of a sensor array 24, conductive connectors 8, and a communication connector 6 of the headgear 1.
Figure 4:
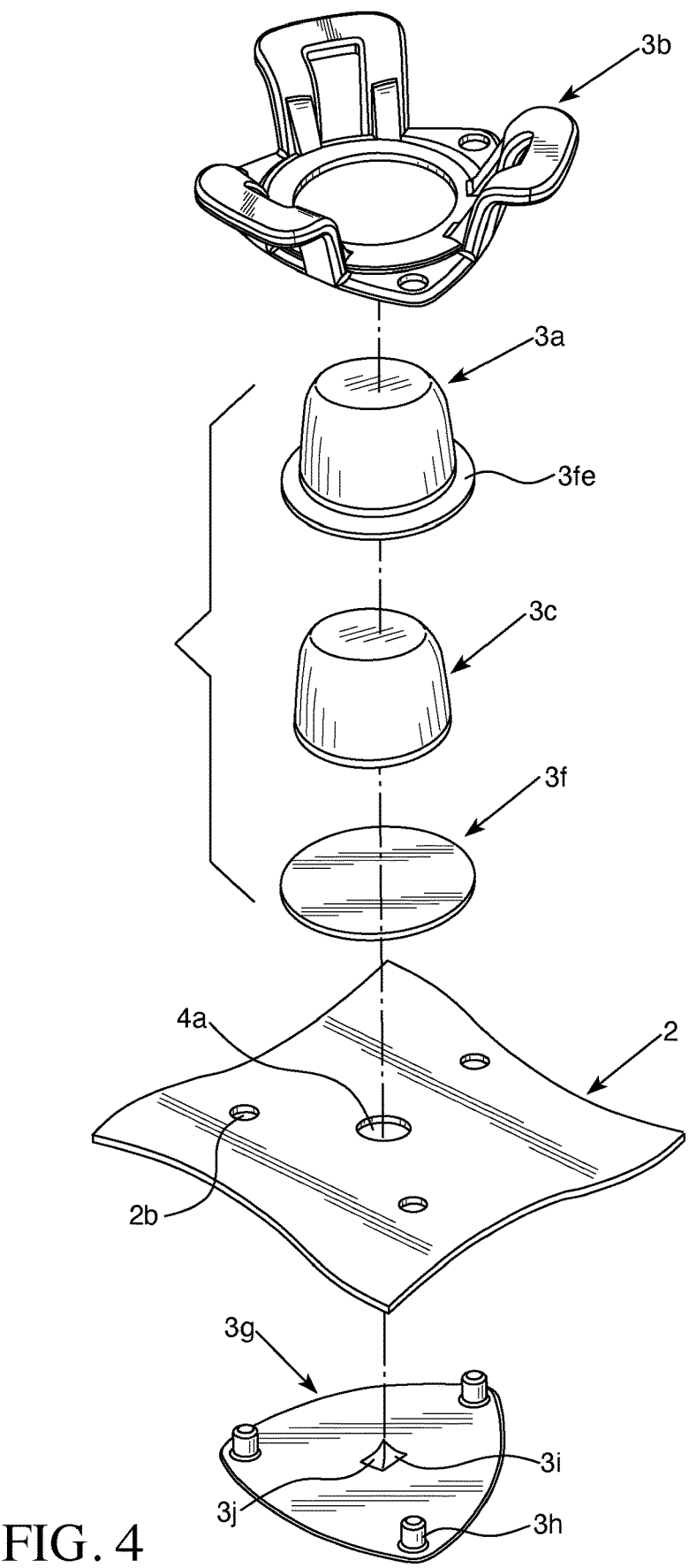
FIG. 4 is an exploded view of the exemplary embodiment of the gel distribution module included in the gel distribution apparatus of the first exemplary embodiment of the headgear 1. It should be appreciated that only a limited portion of the body 2 is shown in FIG. 4 for better illustration of the components of the exemplary gel distribution module.
Figure 5:
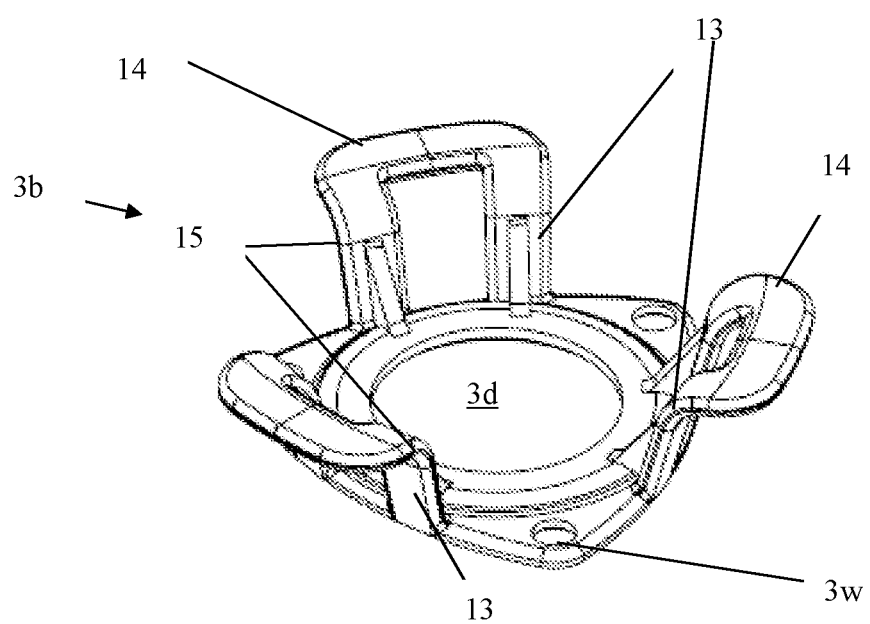
FIG. 5 is a perspective view of an outer component 3b of the exemplary embodiment of the gel distribution module 3 included in the first exemplary embodiment of the headgear 1. As can be seen in FIG. 5, this component has flanges 3c extending away from an inner hole 3d defined by the body of the outer component 3b.
Figure 6:
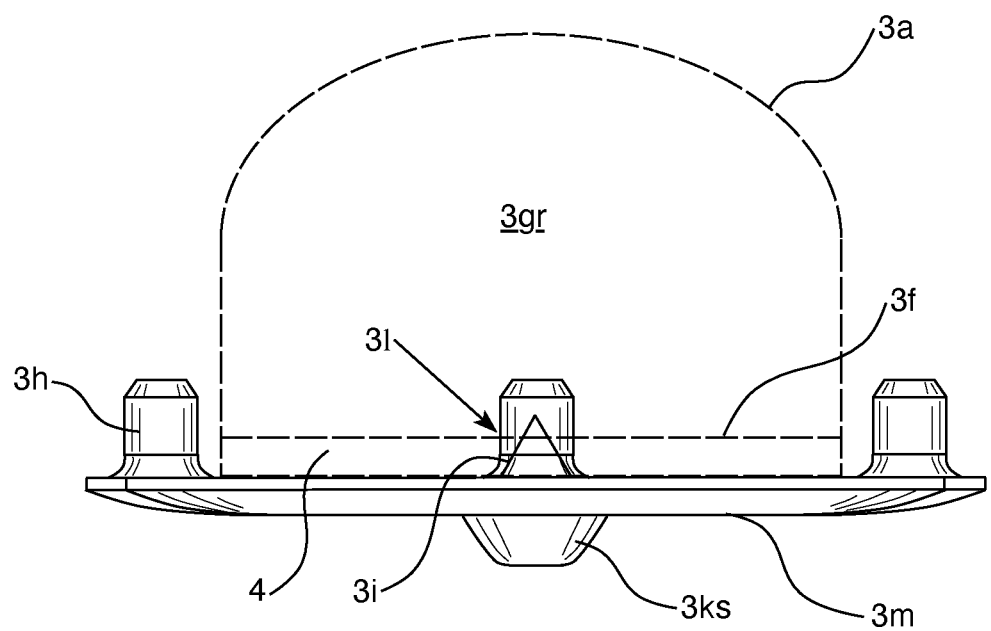
FIG. 6 is a side view of an inner component 3g of the exemplary embodiment of the gel distribution module 3 included in the first exemplary embodiment of the headgear 1.

As may best be seen from FIGS. 3-5, some embodiments of the flanges 3c can be structured to have a generally U-shaped structure in which the handle portion of the generally U-shaped flange structure is bent or folded to angle away from the legs 13 of the generally U-shaped structure and the inner hole 3d defined by the annular body of the outer component 3b. Of course, other embodiments can utilize different shaped flanges or may just have a single unitary flange. In some embodiments, a sidewall may extend around a periphery of the inner hole 3d and define a single leg of the flange, for example. In other embodiments, there may be only two flanges 3c, four flanges 3c, or more than four flanges 3c. Such flanges can be shaped similarly to the exemplary embodiment that may best be seen from FIGS. 3-5 or may have a different structure to meet a particular set of design criteria.

The flanges 3c can preferably be configured to extend to a location that is beyond the outermost portion of the gel receptacle 3a that extends beyond the inner hole 3d and away from the inner component 3g. This can permit the flanges 3c to help protect the gel receptacle 3a and avoid the gel receptacle 3a being inadvertently compressed via a compression force CF that may be applied by accidentally dropping the headgear 1 or gel distribution module 3 on a floor or other surface, for example. For instance, a height of each flange 3c can be greater than a height of the gel receptacle 3a to help provide protection against inadvertent compression of the gel gap 3a and accidental formation of a punctured opening 31 in the gel seal member 3f. If a module having such flanges 3c or such a flange 3c is dropped, the handles 14 of the flanges 3c can first contact a floor or other surface to avoid any force directly acting on the gel receptacle to prevent an unintended compression force CF sufficient to puncture the seal member 3f and open the gel reservoir 3gr from being applied to the gel receptacle 3a due to the accidental dropping of the headgear 1 or gel distribution module 3.

Figure 9:
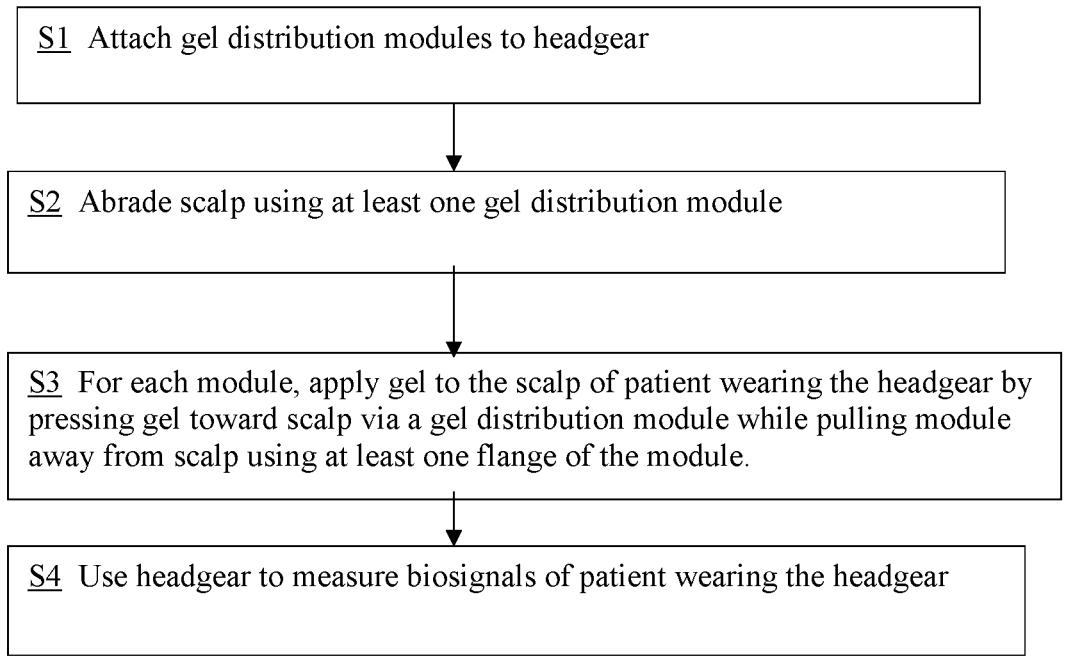
FIG. 9 is a flow chart illustrating an exemplary method of distributing gel onto the scalp of a patient to facilitate formation of a sufficient electrical connection between one or more sensors and the patient's scalp for measuring at least one health metric of the patient via the at least one sensor.
Figure 10:
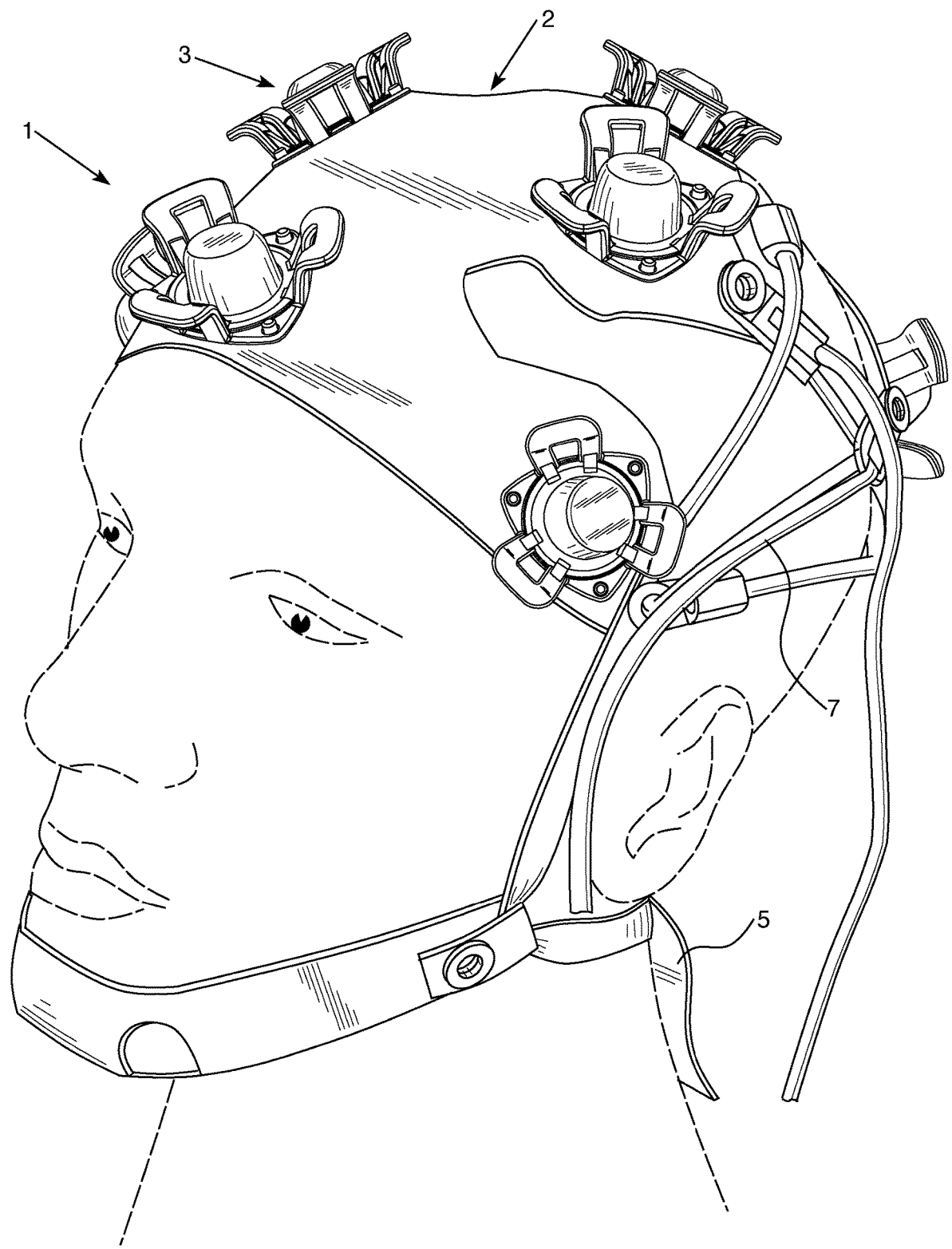
FIG. 10 is an elevated front left side perspective view of the first exemplary embodiment of the headgear 1 being worn by a patient. An elevated front right side perspective view of the first exemplary embodiment of the headgear 1 being worn by a patient would be a mirror image of FIG. 10.
Figure 11:
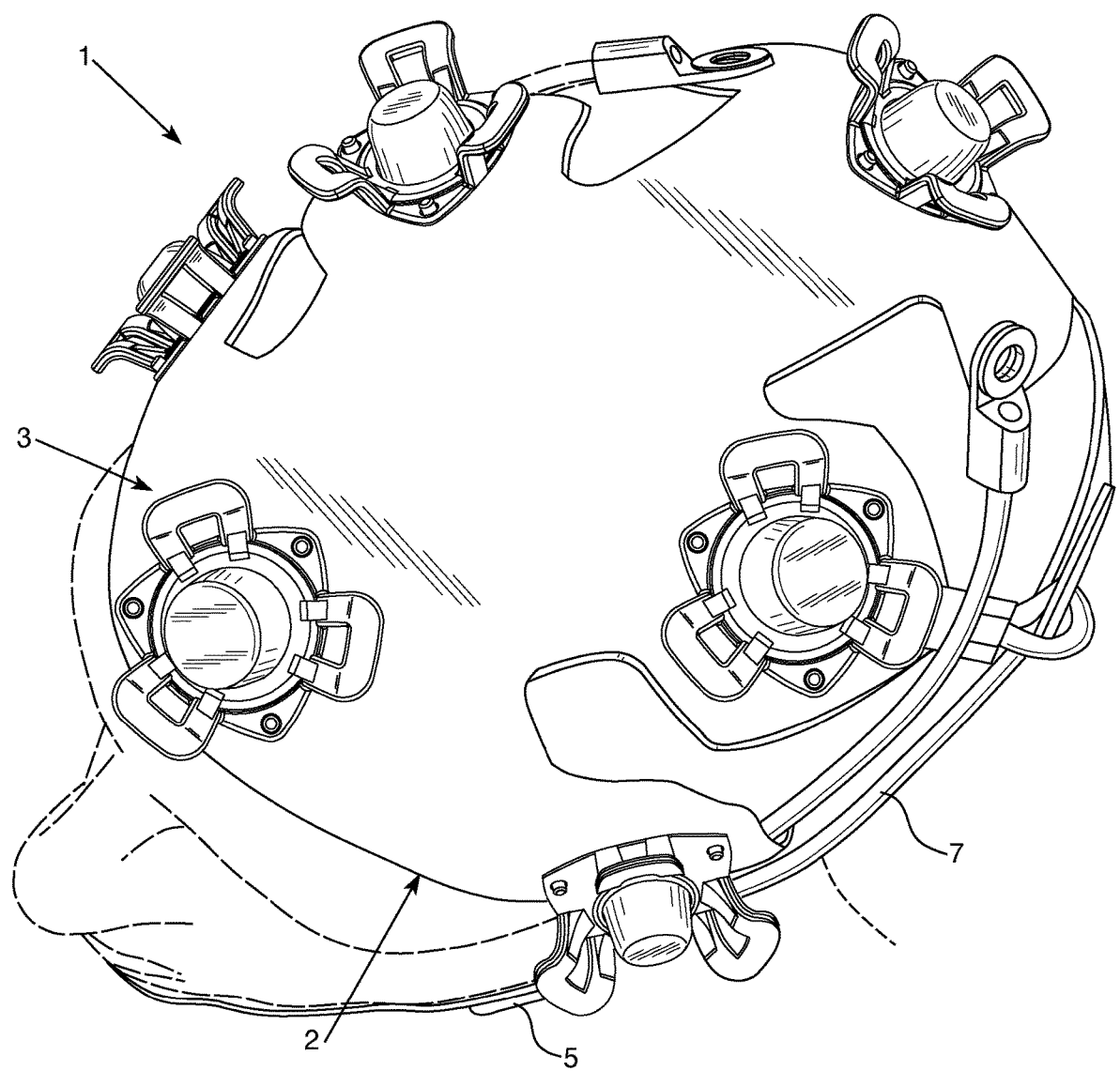
FIG. 11 is a perspective top view of the first exemplary embodiment of the headgear 1 being worn by a patient.
Figure 12:
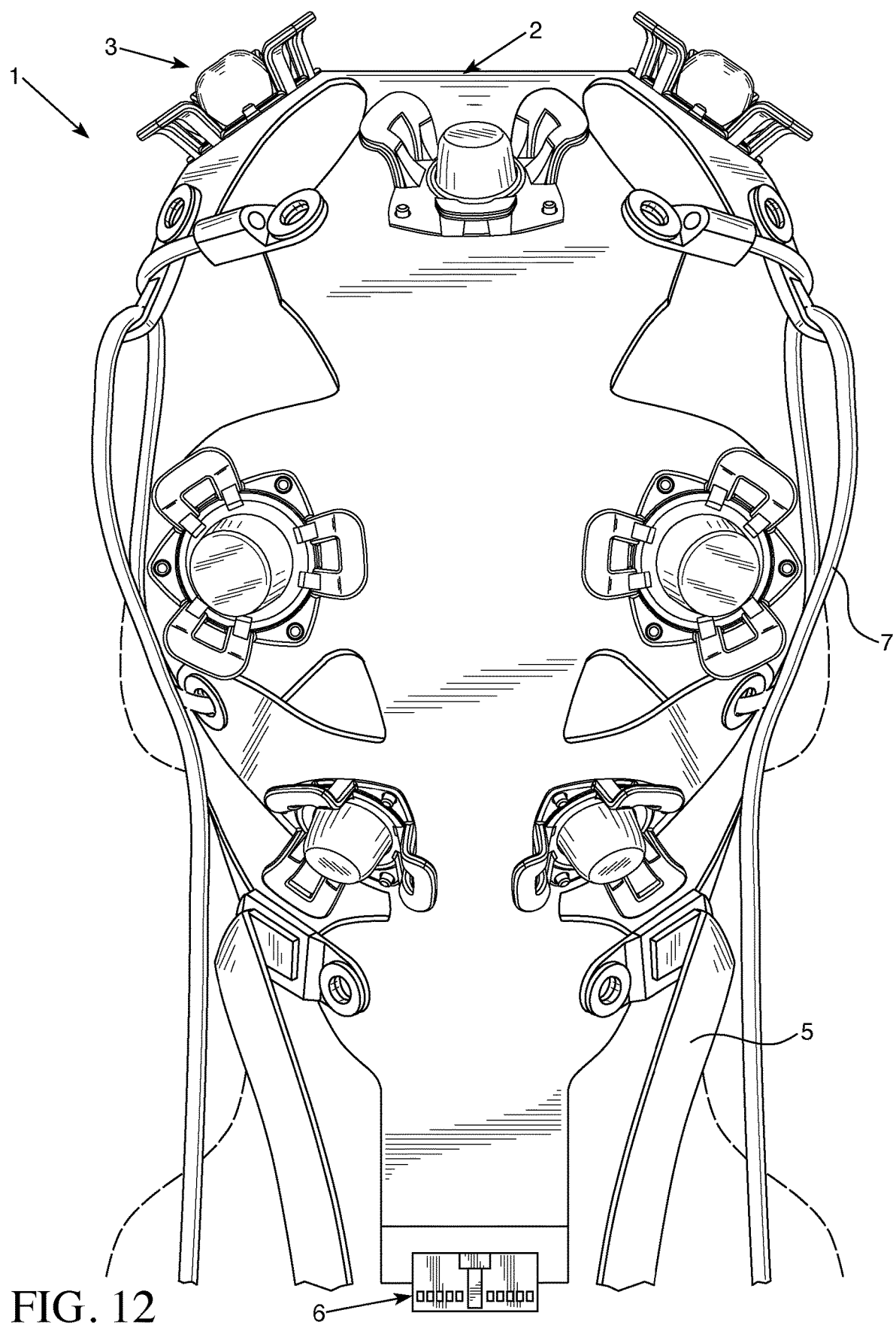
FIG. 12 is a perspective rear view of the first exemplary embodiment of the headgear 1 being worn by a patient.

FIG. 9 illustrates an exemplary method of applying gel onto a patient's head to facilitate measurement of biosignals of the patient that can be taken to help evaluate a medical condition of the patient. Steps of the method can include a first step S1 in which gel distribution modules 3 are attached to the body 2 of the headgear so that each module is positioned adjacent to a sensor 4 of the sensor array 24 such that there is a gel distribution module 3 for a respective sensor 4 for all the sensors 4 of the sensor array 24 or at least a pre-selected number of the sensors 4 of the sensor array 24. The headgear 1 can then be worn by a patient on the patient's head and placed into a desired position on the patient's head.

Thereafter, a user can abrade the scalp of a patient in a second step S2. The abrasion may be performed so that the user abrades one particular location of a scalp before applying gel onto that location. This sequence of abrasion and gel distribution can occur successively for each gel distribution module 3. In other embodiments, the scalp abrasion may occur at each sensor location first and then the gel can be distributed thereafter.

The gel conduit 3k can provide a structure to facilitate abrasion of the scalp S. For instance, the distal end 3y of the gel conduit 3k can be positioned and configured for contacting the scalp by a user providing a pushing force on the gel distribution module 3 to cause the distal end 3y to contact the scalp and rub against the scalp to roughen the skin at the scalp S (e.g. by pushing on one or more flanges 3c to move the distal end 3y of the gel conduit 3k into contact with the skin of the scalp S to apply friction to the skin to roughen the skin). Such abrasion of the skin can roughen the surface of the skin at the scalp so that the surface of the scalp is able to better receive the gel. In some embodiments, the inner component 3g of the gel distribution module 3 can also include other abrasion elements for scalp abrasion in addition to, or as an alternative to, the distal end 3y of the gel conduit 3k.

It should be appreciated that the scalp abrasion can be an optional step. In some embodiments, it may not be necessary to utilize any abrasion of the scalp before applying gel via the gel modules 3.

After the optional abrasion of the scalp is performed, the user can then apply gel from the gel reservoir 3gr of a first gel distribution module 3 of the gel distribution apparatus of the headgear 1 so that gel is applied onto the scalp S and sensor 4 to which the first gel distribution module is adjacently positioned in a third step S3 by providing the compression force CF on the gel receptacle 3a of the first gel distribution module at the same time a pulling force PF is provided on one or more of the flanges 3c to form the punctured opening 31 while also helping to alleviate back pressure that can be created by application of the compression force CF so other unwanted leaks of gel can be avoided. For instance, a user can use two fingers (e.g. pointer finger and middle finger) to grip flanges 3c and provide a pulling force PF while using another finger (e.g. the thumb) to press or push on the gel receptacle to provide the compression force CF. In other embodiments, a user may use one hand to grip the flanges 3c to provide the pulling force PF and a second hand to apply the compression force CF.

This process of scalp abrasion and gel application can be applied successively at each gel distribution module 3 of the headgear 1 until all the gel distribution modules were actuated to apply gel onto the scalp S at the abraded scalp locations. Thereafter, the headgear can be used to measure biosignals of a patient wearing the headgear in a fourth step S4. The headgear 1 can be connected to a computer device to measure the biosignals before the fourth step S4 (e.g. before or after the headgear 1 is worn by the patient), or during the fourth step S4. The computer device can be configured to utilize the data from the sensors 4 to detect a condition of the patient (e.g. detect whether the patient had a stroke or other neurological injury).

It should be appreciated that different embodiments of an electrode array, sensor array, headgear, neurological condition detection device can utilize different arrangements to meet a particular set of design criteria. For example, in some embodiments the gel distribution modules can be configured to include the sensor 4. For instance, the gel seal member 3f, in some embodiments, can be composed of metal and be structured as an electrode or other type of sensor 4. Additionally, or alternatively, the inner component can be conductive or can be coated in a conductive material (e.g. AgCl material) to function as an electrode or other type of sensor 4.

As another example, the sensors 4 and collapsible gel reservoirs 3gr can have bodies of different shapes (e.g. polygonal shaped, oval shaped, dome shaped, etc.). As another example, the size, shape, and configuration of the at least one flange 3c of the gel distribution module can be different from the exemplary arrangements shown in the drawings (e.g. there can be more than three flanges, only two flanges, only a single flange, the one or more flanges can have a different shape or geometry, etc.)

As yet another example, it should be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement. Therefore, while certain exemplary embodiments of headgear, gel distribution mechanisms, gel distribution modules, neurological condition detection mechanisms, and methods of making and using the same have been shown and described above, it is to be distinctly understood that the invention is not limited thereto but may be otherwise variously embodied and practiced within the scope of the following claims.

What is claimed is:

1. A gel distribution module for headgear, the gel distribution module comprising:
    an inner component having a gel conduit defining a gel passageway that extends from a gel inlet opening to a gel outlet opening;
    a gel receptacle having a gel reservoir that is compressible from an initial position to a compressed position in response to application of a compression force;
    an outer component having an annular body that defines an inner hole and at least one flange extending away from the inner hole such that the at least one flange is graspable to apply a pulling force while the compression force is applied to the gel receptacle;
    the gel receptacle positioned to extend from the inner hole, the gel receptacle positioned between the inner component and the outer component;
    the inner component positionable adjacent an inner side of a body of a headgear; and
    the outer component positionable on an exterior side of the body of the headgear for connection with the inner component.

2. The gel distribution module of claim 1, wherein the inner component has a piercing member positioned adjacent to the gel inlet opening configured to form a punctured opening so gel from the gel reservoir is passable from the gel reservoir through the gel inlet opening in response to the compression force meeting or exceeding a puncture threshold.

3. The gel distribution module of claim 2, wherein the at least one flange extends beyond the gel receptacle.

4. The gel distribution module of claim 3, wherein the gel conduit also includes at least one secondary passageway in fluid communication with the gel passageway so that gel is passable through each secondary passageway in a secondary flow direction that is transverse to a primary flow direction of gel passing through the gel passageway 3o to the gel outlet opening.

5. The gel distribution module of claim 1, wherein the gel conduit also includes at least one secondary passageway in fluid communication with the gel passageway so that gel is passable through each secondary passageway in a secondary flow direction that is transverse to a primary flow direction of gel passing through the gel passageway to the gel outlet opening; and
    wherein the inner component has a piercing member positioned adjacent to the gel inlet opening configured to form a punctured opening in a gel seal member attached to the gel receptacle to enclose the gel reservoir so gel from the gel reservoir is passable from the gel reservoir through the gel inlet opening in response to the compression force meeting or exceeding a puncture threshold.

6. Headgear comprising:
    a body having an array of sensors, the body attached to a plurality of gel distribution modules so that each of the gel distribution modules is positioned adjacent to a respective sensor of the array of sensors, each of the gel distribution modules being the gel distribution module of claim 1.

7. A method of applying gel onto a patient to use headgear to measure biosignals of the patient, the method comprising:
    providing headgear having a plurality of sensors and gel distribution modules, each of the gel distribution modules attached to a body of the headgear adjacent a respective sensor of the plurality of sensors;
    applying a compression force to a gel receptacle of a first gel distribution module of the gel distribution modules to form a punctured opening for outputting gel from the gel distribution module to a scalp of the patient wearing the headgear to apply the gel to the scalp of the patient; and
    applying a pulling force that is opposite the compression force on the first gel distribution module via at least one flange of the first gel distribution module at the same time the applying of the compression force is performed.

8. The method of claim 7, wherein each of the gel distribution modules comprise:
    an inner component having a gel conduit defining a gel passageway that extends from a gel inlet opening to a gel outlet opening;
    a gel receptacle having a gel reservoir that is compressible from an initial position to a compressed position in response to application of the compression force;
    an outer component having an annular body that defines an inner hole and at least one flange extending away from the inner hole;
    the gel receptacle positioned to extend from the inner hole, the gel receptacle positioned between the inner component and the outer component;
    the inner component positionable adjacent an inner side of a body of the headgear; and
    the outer component positionable on an exterior side of the body of the headgear for connection with the inner component.

9. The method of claim 8, wherein the at least one flange comprises a plurality of flanges positioned around the gel receptacle, each of the flanges extending beyond the gel receptacle.

10. The method of claim 9, wherein the applying of the pulling force comprises gripping at least two of the flanges to apply the pulling force.

11. The method of claim 10, comprising:
    connecting the headgear to a computer device to use the sensors to measure the biosignals of the patient;

wherein the body of the headgear is comprised of fabric and the headgear also includes at least one strap or cord.

12. The method of claim 8, wherein the inner component has a piercing member positioned adjacent to the gel inlet opening configured to form a punctured opening in a gel seal member positioned to enclose the gel reservoir so gel from the gel reservoir passes from the gel reservoir through the gel inlet opening in response to the compression force meeting or exceeding a puncture threshold.

13. The method of claim 12, wherein the applied compression force meets or exceeds the puncture threshold to form the punctured opening for outputting the gel from the gel reservoir.

14. The method of claim 8, wherein the gel conduit also includes at least one secondary passageway in fluid communication with the gel passageway so that gel is passable through each secondary passageway in a secondary flow direction that is transverse to a primary flow direction of gel passing through the gel passageway to the gel outlet opening.

15. The method of claim 14, wherein the gel that is output from the first gel distribution module passes through the gel passageway and the at least one secondary passageway to contact the scalp and the sensor to which the first gel distribution module is adjacently positioned.

16. The method of claim 8, wherein the applying of the pulling force comprises gripping the at least one flange to pull on the at least one flange to apply the pulling force.

17. The method of claim 8, wherein the at least one flange extends beyond the gel receptacle.

18. The method of claim 8, wherein the headgear includes conductive connectors that connect the sensors to a communication connector.

19. The method of claim 7, comprising:
connecting the headgear to a computer device to use the sensors to measure the biosignals of the patient.

20. The method of claim 19, wherein the sensors measure the biosignals to detect whether the patient experienced a stroke.

* * * * *